United States Patent [19]

Langfeld et al.

[11] Patent Number: 5,606,034
[45] Date of Patent: Feb. 25, 1997

[54] PROCESS FOR THE PREPARATION OF AZO DYES

[75] Inventors: Horst Langfeld, Grenzach-Wyhlen; Karl-Friedrich Haarburger, Lörrach; Herbert Mauser, Grenzach-Wyhlen, all of Germany

[73] Assignee: Ciba-Geigy Corporation, Tarrytown, N.Y.

[21] Appl. No.: 389,371

[22] Filed: Feb. 16, 1995

[30] Foreign Application Priority Data

Feb. 21, 1994 [DE] Germany ............... 44 05 469.6

[51] Int. Cl.⁶ .............. C07C 245/06; C09B 29/08; C09B 29/095
[52] U.S. Cl. .............. 534/573; 534/565; 534/578; 534/579; 534/580
[58] Field of Search .................... 534/565, 580, 534/573, 578, 579

[56] References Cited

U.S. PATENT DOCUMENTS

| | | |
|---|---|---|
| 4,233,213 | 11/1980 | Breig et al. . |
| 4,265,810 | 5/1981 | Bauman et al. . |
| 4,297,278 | 10/1981 | Nickel . |
| 4,874,847 | 10/1989 | Oxenius et al. . |
| 4,918,168 | 4/1990 | Stepanivk et al. . |

FOREIGN PATENT DOCUMENTS 0001236  4/1979  European Pat. Off. .

*Primary Examiner*—Joseph McKane
*Assistant Examiner*—John Peabody
*Attorney, Agent, or Firm*—Kevin T. Mansfield

[57] ABSTRACT

The invention discloses a process for the preparation of azo dyes using an aminodiphenylamine as diazo component. The process comprises reacting the amine, an alkali metal nitrite and a mineral acid continuously in the temperature range from 35° to 65° C. to give the diazo compound, using a 3 to 15% excess of alkali metal nitrite, and thereafter coupling the diazo compound to a coupling component. Azo dyes of superior quality constancy and in high yield are obtained by the novel process.

13 Claims, No Drawings

PROCESS FOR THE PREPARATION OF AZO DYES

The present invention relates to a process for the preparation of azo dyes by diazotising an aromatic amine and coupling the diazo compound to a coupling component, which process comprises carring out the diazotisation continuously.

The diazotisation of aromatic amines, especially of aminodiphenylamines and certain heterocyclic amines, is associated with difficulties that are usually overcome in practice by using the method of indirect diazotisation, which comprises adding an aqueous alkaline solution, warmed to c. 80° C., of the mixture of amine and alkali metal nitrite to an ice-cooled aqueous solution of a mineral acid. An approximately 5 to 7% excess of nitrite is used in this process.

This procedure too, however, has drawbacks. As the reaction begins at c. 0° C., the amine precipitates in the form of tacky agglomerates the complete diazotisation of which—owing to insufficient reactant contact—can only be effected by stirring for several hours in the temperature range from c. 60°–65° C. This results in partial decomposition of the diazo compound, the reactor being subjected to severe stress owing to the great differences in temperature and to the concentrated $NO_x$ atmosphere at elevated temperature, and also in contamination of the waste air caused by the emission of $NO_x$. It is necessary to add large amounts of ice for, and after completion of, the diazotisation to prepare for the coupling, resulting in unwanted dilution of the reaction solution and in very unsatisfactory space/time yields.

EP-A-0 001 236 discloses a process for the continuous diazotisation of aromatic amines in which a partial stream of the mixture of amine and nitrite is passed through an analyser where the nitrite excess is measured. This measurement is used for controlling the addition of nitrite to the receiver vessel. This procedure, however, requires complicated apparatus for analysing the excess of nitrite. In addition, controlling the reaction by way of the excess nitrite is not reliable in the case of aminodiphenylamines owing to the resultant secondary nitrosation.

It has now been found that it is possible to diazotise aromatic amines of formula I below in simple manner by carrying out the diazotisation continuously in the temperature range from c. 35° to 65° C. Surprisingly, the diazo compound is sufficiently stable and a complicated control of the nitrite excess is not necessary, as excess nitrite can subsequently be easily destroyed, conveniently by adding sulfamic acid. The subsequent conventional coupling affords dyes of excellent quality and in improved yield. The dyes contain no more sec-NO groups detectable by known methods. The quality constancy of the dyes is also surprisingly high. There are only minor variations of shade within the accepted standard conformity, so that in the final standardisation step expensive corrective measures are no longer necessary. Such measures are unavoidable in the known processes, as there the shade of the resultant dyes varies greatly, even if there are only minimal inevitable deviations in the reaction conditions such as temperature, pH, stirring speed and the like. Further advantages of the novel process are the mild conditions in the reactors owing to minor temperature differences and low $NO_x$ content, as well as the energy-saving mode of reaction and simultaneously a high space-time yield.

Accordingly, the invention relates to a process for the preparation of azo dyes, starting from an amine of formula

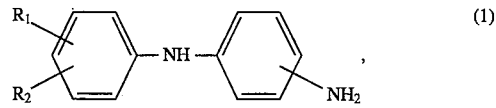

wherein $R_1$ is hydrogen or nitro, and $R_2$ is hydrogen, sulfo, $C_1$–$C_4$alkyl or $C_1$–$C_4$alkoxy, which comprises reacting the amine, an alkali metal nitrite and a mineral acid continuously, in the temperature range from 35° to 65° C., to give the diazo compound, using a 3 to 15% excess of the alkali metal nitrite, and subsequently coupling the diazo compound to a coupling component.

$R_1$ is preferably nitro, more particularly nitro in p-position to the NH group.

The preferred meaning of $R_2$ is hydrogen or, more particularly, sulfo.

It is very particularly preferred to use an amine of formula

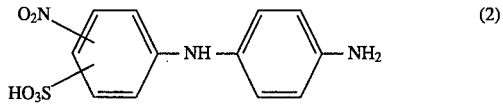

and it is especially preferred to use 4'-amino-4'-nitrodiphenylamine-2-sulfonic acid as aromatic amine.

The cited amines are used in the form of aqueous solutions or suspensions. It is preferred to dissolve the amines completely by suspending them in water and adding a base, conveniently KOH or NaOH, and heating to c. 40°–90° C.

The alkali metal nitrite will typically be potassium nitrite or, preferably, sodium nitrite; and the mineral acid will typically be sulfuric acid or, preferably, hydrochloric acid.

A 2 to 15%, preferably a 5 to 10%, excess of alkali metal nitrite is used, based on the amine of formula (1).

It is preferred to add about 2.5 mol of mineral acid per mol of amine.

Diazotisation is carried out in a commercially available continuous flow reactor which is preferably fitted with a mixer for very intensive mixing of the components. The procedure comprises e.g. running in the amine, alkali metal nitrite and mineral acid e.g. through three separate feed lines synchronously in the requisite amounts. However, it is also possible to mix two of the components, conveniently amine and alkali metal nitrite, with each other before they are introduced into the flow reactor.

The reaction temperature is in the range from 35° to 65° C., preferably from 40 to 55° C.

The residence time in the flow reactor will depend, inter alia, on the type of aromatic amine and on the temperature. Usually it is from about 0.1 to 10 minutes, preferably from about 0.5 to 5 minutes.

After exiting from the flow reactor, the solution of the diazo component is cooled, if necessary, and coupled to a coupling component, preferably batchwise.

When the reaction mixture exits the reactor and prior to coupling, it is preferred to destroy any nitrite still present. This is done in known manner, typically by addition of sulfamic acid or urea.

Coupling is effected in conventional manner with the customary coupling components used for the preparation of azo dyes. As the amines of formula (1) are preferably used for the preparation of leather dyes, particularly suitable coupling components are phenols, naphthols, anilines and naphthylamines which may carry further substituents such as nitro, sulfo, alkyl, alkoxy or arylazo. Also suitable are the customary fustic extracts for leather dyes, for example the polyhydroxy compounds such as maclurin, morin or quercetin.

The dye is subsequently isolated in conventional manner, typically by salting out or by concentrating the reaction mixture in suitable apparatus.

In addition to the preparation of azo dyes starting from aminodiphenylamine as diazo component, the novel process is also preeminently suitable for the preparation of azo dyes with heterocyclic diazo components. Illustrative examples are: 2-aminobenzothiazole, 6-nitro-2-aminobenzothiazole, 6-benzoyl-2-aminobenzothiazole, 6-methyl-2-aminobenzothiazole, 6-methoxy-2-aminobenzothiazole, 2-aminotriazole, 5-methylsulfonyl-2-aminotriazole, 5-nitro-2-aminotriazole, 3-amino-1,2,4-triazole, 3-aminoindazole, 5-aminoindazole, 4-aminoquinoline and aminobenzimidazole derivatives.

The monoazo and polyazo dyes obtainable by the process of this invention are isolated in per se known manner, conveniently in the form of their salts, preferably alkali metal salts, more particularly sodium or potassium salts, or ammonium salts.

The dyes obtainable by the novel process are anionic dyes that are readily soluble in water and suitable for dyeing textile and non-textile substrates that are dyable with anionic dyes, e.g. for dyeing fibre materials of natural or regenerated cellulose such as cotton, synthetic polyamides such as nylon, wool, silk, polyurethanes or basic-modified polyolefins, and preferably, for dyeing leather.

The dyeings obtainable with the dyes prepared by the process of this invention are distinguished by good application and tinctorial properties, typically including good fastness to light, water, washing, persipiration, dry cleaning, acid, alkali and solvents, and good diffusion fastness to plasticised PVC, good resistance to electrolytes such as sodium or calcium salts and to iron, chromium, cobalt or copper salts, and good build-up on pure chrome-tanned leather and retanned leather.

The invention is illustrated by the following non-limitative Examples in which parts and percentages arc by weight.

EXAMPLE 1

309 parts of 4'-amino-4-nitrodiphenylamine-2-sulfonic acid (95%) are suspended in 2700 parts of water at c. 70° C. and completely dissolved by adding c. 90 parts of a 50% solution of NaOH and heating to c. 80° C. The amine solution is then cooled adiabatically or indirectly and diazotised in a continuous flow reactor at 47°–50° C. Then 424 parts of 32% hydrochloric acid and 172 parts of a 46% aqueous solution of sodium nitrite are run into the reactor synchronously with the amine solution. The reactor is fitted with a high-speed mixer for very good micromixing. The flow time is 0.9 minute. The amine is completely diazotised when it exits the reactor.

The resultant diazo suspension is cooled over an indirect heat exchanger to c. 35° C. and collected in a receiver vessel over an ice/water mixture in the presence of c. 3 parts of sulfamic acid, whereupon the temperature of the diazo mixture falls to 0° C. The cooled diazonium salt is then added at about pH 8.6 in alkaline medium buffered with sodium carbonate to the coupling product, obtained in known manner, from 170 parts of diazotised 1-amino-8-naphthol-3,6-disulfonic acid and 55 parts of resorcinol. The reaction is carried out adiabatically, such that the temperature, after initially cooling the reaction mixture with ice to 5° C., can rise freely to 18° C. The pH is kept constant by addition of NaOH solution.

The dye is salted out in conventional manner by addition of NaCl in strongly acidic medium, isolated and dried, affording about 915 parts of dry powder that dyes leather by standard dyeing methods in a dark brown shade.

A 12–15% higher dye yield, based on 4'-amino-4-nitrodiphenylamine-2-sulfonic acid, is obtained than in conventional batch production, as virtually no decomposition of the diazo component occurs prior to coupling.

The dye contains no more sec-NO groups detectable by known methods. The quality constancy of the dye is surprisingly high. There are only minor variations of shade within the accepted standard conformity, so that in the final standardisation step expensive corrective measures are no longer necessary. Such measures are unavoidable in the known processes, as there the shade of the resultant dyes varies greatly, even if there are only minimal inevitable deviations in the reaction conditions such as temperature, pH, stirring speed and the like. EXAMPLE 2

In accordance with the same general procedure as described in Example 1, a brown dye is prepared by first diazotising 4'-amino-4-nitrodiphenylamine-2-sulfonic acid, coupling the diazo compound to the equivalent amount of 1-aminonaphthalene-6-sulfonic acid, diazotising the resultant azo dye and coupling to the equivalent amount of resorcinol and, finally, coupling the disazo dye so obtained to an equivalent amount of diazotised 4'-amino-4-nitrodiphenylamine-2-sulfonic acid, the diazotisation of 4'-amino-4-nitrodiphen- ylamine-2-sulfonic acid and the subsequent coupling being carried out as described in Example 1.

The brown dye is obtained in good yield and, in different batches, in constant shade.

EXAMPLE 3

In accordance with the same general procedure as described in Example 1, a brown dye is prepared by first diazotising 220 parts of aniline-2,5-disulfonic acid and coupling the diazo compound to 670 pans of a mixture comprising mainly the compounds bearing the Colour Index Constitution Numbers, C.I. 75240 and 75660 in the COLOUR INDEX, then coupling to the reaction product the diazonium compound from 160 parts of 4-nitroaniline and afterwards the diazonium compound from 230 parts of 4'-amino-4-nitrodiphenylamine-2-sulfonic acid, the diazotisation of 4'-amino-4-nitrodiphenylamine-2sulfonic acid and the subsequent coupling being carried out as described in Example 1.

The brown dye is obtained in good yield and, in different batches, in constant shade.

EXAMPLE 4

In accordance with the same general procedure as described in Example 1, a brown dye is prepared by first diazotising 200 pans of 1-aminonaphthalene-5-sulfonic acid (93%) and coupling the diazo compound to 450 parts of a mixture comprising mainly the compounds bearing the Colour Index Constitution Numbers, C.I. 75240 and 75660 in the COLOUR INDEX, then coupling to the reaction product the diazonium compound from 155 parts of 4-nitroaniline and afterwards the diazonium compound from 230parts of 4'-amino-4-nitrodiphenylamine -2-sulfonic acid, the diazotisation of 4'-amino-4-nitrodiphenylamine-2-sulfonic acid and the subsequent coupling being carried out as described in Example 1.

The brown dye is obtained in good yield and, in different batches, in constant shade.

EXAMPLE 5

In accordance with the same general procedure as described in Example 1, a brown dye is prepared by first diazotising 310 parts of 1-hydroxy-8-aminonaphthalene-3, 6-sulfonic acid (98%) and coupling the diazo compound to 115 parts of resorcinol, then coupling to the reaction product the diazonium compound from 130 parts of 4-methoxyaniline and afterwards the diazonium compound from 465 parts of 4'-amino-4-nitrodiphenylamine-2-sulfonic acid, the diazotisation of 4'-amino-4-nitrodiphenylamine-2-sulfonic 2-sulfonic acid and the subsequent coupling being carried out as described in Example 1.

The brown dye is obtained in good yield and, in different batches, in constant shade.

EXAMPLE 6

In accordance with the same general procedure as described in Example 1, a brown dye is prepared by first diazotising 590 parts of 4'-amino-4-nitrodiphenylamine-2-sulfonic acid (96%) and coupling the diazo compound to 440 parts of a mixture of 1-aminonaphthalene-6-sulfonic acid and 1-aminonaphthalene-7-sulfonic acid, then diazotising the reaction product and coupling it to 160 parts of phenol and, finally, tosylating the reaction product with 387 parts of p-toluenesulfonic acid, the diazotisation of 4'-amino-4-nitrodiphenylamine-2-sulfonic acid and the subsequent coupling being carried out as described in Example 1.

The brown dye is obtained in good yield and, in different batches, in constant shade.

EXAMPLE 7

In accordance with the same general procedure as described in Example 1, a brown dye is prepared by first diazotising 190 parts of 2-hydroxy-3-nitroaniline-5-sulfonic acid and coupling the diazo compound to 100 parts of resorcinol, then coupling the diazonium compound from 100 parts of 4'-amino-4-nitrodiphenylamine-2-sulfonic acid to the reaction product, afterwards coupling to the reaction product the diazonium compound from 100 parts of 4-nitroaniline and, finally, the diazonium compound from 215 parts of 4'-amino-4-nitrodiphenylamine-2-sulfonic acid, the diazotisation of 4'-amino-4-nitrodiphenylamine-2-sulfonic acid and the subsequent coupling being carried out as described in Example 1. The reaction product so obtained is subsequently converted into the copper complex with copper sulfate in conventional manner.

The brown dye is obtained in good yield and, in different batches, in constant shade.

What is claimed is:

1. A process for the preparation of an azo dye, starting from an amine of formula

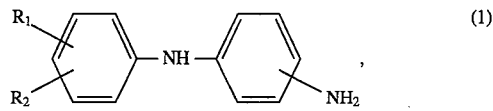

wherein $R_1$ is hydrogen or nitro, and $R_2$ is hydrogen, sulfo, $C_1$–$C_4$alkyl or $C_1$–$C_4$alkoxy, which comprises reacting the mine, an alkali metal nitrite and a mineral acid continuously, in the temperature range from 35° to 65° C., to give the diazo compound, using a 3 to 15% excess of the alkali metal nitrite, and subsequently coupling the diazo compound to a coupling component.

2. A process according to claim 1, which comprises diazotising an amine of formula (1), wherein $R_1$ is nitro.

3. A process according to claim 1, which comprises diazotising an amine of formula (1), wherein $R_2$ is hydrogen or sulfo.

4. A process according to claim 1, which comprises diazotising an amine of formula

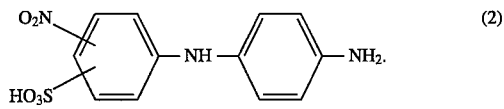

5. A process according to claim 4, which comprises diazotising 4'-amino-4-nitrodiphenylamine-2-sulfonic acid.

6. A process according to claim 1, which comprises using the amine to be diazotised as an aqueous solution obtained by suspending the amine in water and adding a base and heating to about 40°–90° C.

7. A process according to claim 6, wherein the base is KOH or NaOH.

8. A process according to claim 1, wherein the alkali metal nitride is potassium or sodium nitrite.

9. A process according to claim 1, wherein a 5 to 10% excess of alkali metal nitrite is used, based on the amine.

10. A process according to claim 1, wherein the diazotisation is carried out in the temperature range from 40° to 55° C.

11. A process according to claim 2, wherein $R_1$ is in the para-position to the NH group.

12. A process according to claim 1 which is carried out in a flow reactor.

13. A process according to claim 12, wherein the residence time in the flow reactor is from 0.1 to 10 minutes.

* * * * *